(12) United States Patent
Cloninger et al.

(10) Patent No.: US 8,329,155 B2
(45) Date of Patent: Dec. 11, 2012

(54) QUATERNARY AMMONIUM FUNCTIONALIZED GLYCODENDRIMERS, METHODS FOR THE PRODUCTION AND USE THEREOF

(75) Inventors: Mary Cloninger, Bozeman, MT (US); Robert Engel, Carle Place, NY (US)

(73) Assignees: Montana State University, Bozeman, MT (US); Queen's College of the City University of New York, Flushing, NY (US)

( * ) Notice: Subject to any disclaimer, the term of this patent is extended or adjusted under 35 U.S.C. 154(b) by 899 days.

(21) Appl. No.: 12/282,496

(22) PCT Filed: Mar. 12, 2007

(86) PCT No.: PCT/US2007/006213
§ 371 (c)(1),
(2), (4) Date: Jan. 8, 2009

(87) PCT Pub. No.: WO2007/106437
PCT Pub. Date: Sep. 20, 2007

(65) Prior Publication Data
US 2009/0196847 A1    Aug. 6, 2009

Related U.S. Application Data

(60) Provisional application No. 60/780,860, filed on Mar. 10, 2006.

(51) Int. Cl.
*A61K 31/00* (2006.01)
(52) U.S. Cl. .................................... 424/78.17
(58) Field of Classification Search .......... None
See application file for complete search history.

(56) References Cited

U.S. PATENT DOCUMENTS

| 6,224,898 | B1 | 5/2001 | Balogh et al. | |
|---|---|---|---|---|
| 6,440,405 | B1 * | 8/2002 | Cooper et al. | 424/78.17 |
| 7,097,856 | B2 | 8/2006 | Frechet et al. | |
| 7,148,293 | B2 | 12/2006 | Stumbe et al. | |
| 7,214,546 | B2 | 5/2007 | Sparks | |
| 2003/0180250 | A1 * | 9/2003 | Chauhan et al. | 424/78.05 |
| 2006/0188537 | A1 | 8/2006 | Lamba-Kohli | |
| 2007/0071713 | A1 | 3/2007 | Mahmud | |
| 2007/0122441 | A1 | 5/2007 | Murata et al. | |

OTHER PUBLICATIONS

International Search Report with Written Opinion, issued in International Appln. No. PCT/US07/06213 on Sep. 5, 2008.

* cited by examiner

*Primary Examiner* — Anand Desai
*Assistant Examiner* — Melissa Mercier
(74) *Attorney, Agent, or Firm* — Cooley LLP

(57) ABSTRACT

The present invention provides novel antimicrobial agents that are quaternary ammonium functionalized glycodendrimers. In one embodiment, the quaternary ammonium functionalized glycodendrimers are compounds of Formula (I): $(Q^{+}\text{-}S\text{-}L)_z\text{-}D_n X^-$ wherein: D is a dendrimer; n is the generation number of the functionalized dendrimer; z is an integer less than or equal to $2^{(n+2)}$; L is a linking group; $Q^+$ represents a quaternary ammonium moiety; and S represents a carbohydrate moiety. The present invention further provides formulations containing the antimicrobial agents of the invention, methods of making the agents and formulations of the invention, and methods of using the same as effective and/or broad spectrum antimicrobial agents. The agents and formulations of the invention find use in medicine, for the treatment of various inflammatory conditions or diseases, for example, and have numerous industrial applications.

$$(Q^{+}\text{-}S\text{-}L)_z\text{-}D_n X^- \qquad (I)$$

33 Claims, No Drawings

QUATERNARY AMMONIUM FUNCTIONALIZED GLYCODENDRIMERS, METHODS FOR THE PRODUCTION AND USE THEREOF

This application is a National Stage of PCT/US2007/006213, filed Mar. 12, 2007, which claims the benefit of U.S. Provisional Application No. 60/780,860, filed Mar. 10, 2006, each of which are hereby incorporated by reference in their entirety.

STATEMENT REGARDING FEDERALLY SPONSORED RESEARCH OR DEVELOPMENT

This invention was supported in part by funds obtained from the U.S. Government (NIGMS 62444), and the U.S. Government may therefore have certain rights in the invention.

BACKGROUND OF THE INVENTION

While quaternary ammonium compounds are widely used as disinfectants, more potent and/or broader spectrum antimicrobials are desperately needed. For example, small molecule quaternary ammonium compounds are generally ineffective against Gram-negative bacteria, such as E. coli, since these microbes have very sophisticated outer membrane structures that effectively keep out antibacterial agents.

In addition to a cationic site, a significant lipophilic component enhances antimicrobial action. The mechanism of action of these cationic surfactants on bacteria is believed to be one of electrostatic interaction and physical disruption, rather than interference with a metabolic pathway. The cationic site of the agent is able to bind to anionic sites of the cell wall surface. With the lipophilic component present, the agent is then able to disrupt the membrane and permit release of electrolytes and nucleic materials, leading to cell death.

SUMMARY OF THE INVENTION

The present invention provides novel antimicrobial agents that are quaternary ammonium functionalized glycodendrimers. The quaternary ammonium functionalized glycodendrimers comprise a plurality of carbohydrate and quaternary ammonium substituents covalently linked to a dendrimer. For example, the glycodendrimer of the invention may contain quaternary ammonium substituents each linked to a carbohydrate substituent, with each carbohydrate substituent being linked to the dendrimer though a linking group.

Dendrimers are unique, highly branched, organic molecules that have uniform size and three-dimensional structures, and can be synthesized to have various internal structures and various surface properties. Because of the multiple reaction sites on the dendrimer molecules, dendrimers can be functionalized by the addition of various end groups.

In one embodiment, the quaternary ammonium functionalized glycodendrimers of the invention are compounds of Formula (I):

$$(Q^{+-}\text{-S-L})_z\text{-}D_n X^- \quad (I)$$

wherein:
D is a dendrimer;
n is the generation number of the functionalized dendrimer selected from the group consisting of 1, 2, 3, 4, 5, 6, 7, 8, 9, 10, 11, 12, 13, 14, and 15;
z is an integer less than or equal to $2^{(n+2)}$;
L is a linking group;
$Q^+$ represents a quaternary ammonium moiety; and
S represents a carbohydrate moiety.

The present invention further provides formulations containing the antimicrobial agents of the invention, methods of making the agents and formulations of the invention, and methods of using the same as effective and/or broad spectrum antimicrobial agents. The agents and formulations of the invention find use in medicine, for the treatment of various inflammatory conditions or diseases, for example, and have numerous industrial applications.

DETAILED DESCRIPTION OF THE INVENTION

All publications and patent applications cited herein are incorporated by reference to the same extent as if each individual publication or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Quaternary Ammonium Functionalized Glycodendrimers

The present invention provides quaternary ammonium functionalized glycodendrimers as antimicrobial agents, the quaternary ammonium functionalized glycodendrimers comprising a plurality of carbohydrate and quaternary ammonium substituents covalently linked to a dendrimer. For example, the glycodendrimer of the invention may have each quaternary ammonium substituent linked to a carbohydrate substituent, with each carbohydrate substituent being linked to the dendrimer through a linking group.

The terms "glycodendrimer" or "carbohydrate functionalized dendrimer" include: dendrimers that having more than one species of carbohydrate moiety covalently linked to one species of dendrimer, dendrimers that comprise one species of carbohydrate covalently linked to a mixture of species of dendrimers, and dendrimers that comprise more than one species of carbohydrate moiety covalently linked to a mixture of species of dendrimers.

Dendrimers are well defined, highly branched macromolecules that emanate from a central core, and provide a high number of functional groups in a compact space. Commercially available dendrimers include polyamidoamine (PAMAM) dendrimers and polypropylene imine (PPI) dendrimers. Exemplary dendrimers include polyamidoamine dendrimers, polylysine-based dendrimers, polyethylene oxide-based dendrimers, silicon-based dendrimers, polyether-based dendrimers, and polypropylene imine dendrimers. A polylysine-based dendrimer refers to a dendrimer in which the backbone or structure consists essentially of polylysine. A polyethylene oxide-based dendrimer refers to a dendrimer in which the backbone or structure consists essentially of polyethylene oxide. A silicon-based dendrimer refers to a dendrimer in which the backbone or structure consists essentially of silicon. A polyether-based dendrimer refers to a dendrimer in which the backbone or structure consists essentially of polyether.

The present invention also contemplates as dendrimers, hyperbranched polymers that can be prepared using a one-pot synthesis. These are typically polydisperse, structurally imperfect, and better positioned for industrial applications. Hyperbranched polymers can be for example polyethylene oxide-based hyperbranched polymers, polyglycerol-based hyperbranched polymers, and silicon-based hyperbranched polymers. A polyethylene oxide-based hyperbranched polymer refers to a hyperbranched polymer in which the backbone or structure consists essentially of polyethylene oxide. A polyglycerol-based hyperbranched polymer refers to a hyperbranched polymer in which the backbone or structure consists essentially of polyglycerol. A silicon based hyperbranched polymer refers to a hyperbranched polymer in which the backbone or structure consists essentially of silicon. Commercially available Hyperbranched polymers include Polyols from Perstop Inc., which exemplifies hyperbranched polyols, and Hybrane™ from DSM. "Hybrane" as used herein refers to the commercially available Hybrane™ from DSM.

In one embodiment, the invention provides a glycodendrimer of the following Formula (I):

$$(Q^+\text{-}S\text{-}L)_z\text{-}D_nX^-  \qquad (I)$$

wherein
D is a dendrimer;
n is the generation number of the functionalized dendrimer selected from the group consisting of 1, 2, 3, 4, 5, 6, 7, 8, 9, 10, 11, 12, 13, 14, and 15;
z is an integer less than or equal to $2^{(n+2)}$;
L is a linking group;
$Q^+$ represents a quaternary ammonium moiety; and
S represents a carbohydrate moiety.

The variable "D" as used herein refers to dendrimers that are highly branched macromolecules that emanate from a central core as well as hyperbranched polymers. D may be, for example, a polyamidoamine dendrimer, a polylysine-based dendrimer, a polyethylene oxide-based dendrimer, a silicon-based dendrimer, a polypropylene imine dendrimer, a polyether dendrimer, a polyethylene oxide-based hyperbranched polymer, a polyglycerol-based hyperbranched polymer, a silicon-based hyperbranched polymer, a hyperbranched polyol, and Hybrane™ from DSM (Geleen, Netherlands).

The variable "n" represents the generation of the Dendrimer D. Therefore $D_1$, $D_2$ or $D_3$ represent dendrimers of generation 1, 2, and 3, respectively. In certain embodiments, the invention employs dendrimers of a generation greater than 4, and preferably dendrimers of from generation 4 to generation 8, such as generation 5 or generation 6 dendrimers. In a preferred embodiment of the invention, the dendrimer is of a sufficient size to effect glycoside clustering, that is, the glycodendrimer is sufficiently large to bind multivalently to the target microbe. In this respect, dendrimers having a size of from about 20 to about 35 angstroms are desirable, corresponding to generations 4-6 with PAMAM dendrimers.

The variable "z" represents the number of surface functional groups for a dendrimer. The surface functional groups may be, for example, $-NH_2$, $-OH$, $-COOH$, or CN. As the generation, n, of any dendrimer increases, the number of surface functional groups, z, also increases. A generation 1 dendrimer, $D_1$, may have as many as many as eight surface functional groups ($2^3$), while a generation 2 dendrimer, $D_2$, may have a many as sixteen surface functional groups ($2^4$). The maximum number of functional groups is represented by the letter z when it is equal to $2^{n+2}$ where n is equal to the generation of a given dendrimer. Because a given dendrimer may have less than the maximum number of possible surface groups functionalized, the actual number of functionalized groups on a given dendrimer is less than or equal to $2^{n+2}$.

The variable "L" represents a linking group that links the carbohydrate group to the surface group of the Dendrimer (D). The linking group L can be either rigid or flexible. The linking group L can be, for example, an alkyl, an alkenyl, an alkynyl or aryl group. Exemplary linking groups also include $-NH-C(S)-NH-CH_2-CH_2-O-CH_2-CH_2-O-$, $-CO-NH-CH_2-CH_2-$, $-CO-NH-CH_2-$, $-CO-NH-CH_2-CH_2-CH_2-$, $-CO-NH-CH_2-CH_2-CH_2-CH_2-$, $-CO-NH-CH_2-CH_2-CH_2-CH_2CH_2-$, $-CO-NH\text{-Phenyl-}CH_2-$, $-CO-NH-CH_2-CH_2-O-CH_2-CH_2-$, $-(CH_2)-$, $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$, $-(CH_2)_{10}-$, $-(CH_2)_{11}-$, $-(CH_2)_{12}-$, $-(CH_2)_{13}-$, $-(CH_2)_{14}-$, $-(CH_2)_{15}-$, $-(CH_2)_{16}-$, $-(CH_2)_{17}-$, $-(CH_2)_{18}-$, $-(CH_2)_{19}-$, $-(CH_2)_{20}-$, as well as similar physiochemical structures. The linking group is at least one carbon atom in length, and may be a C1-20 straight, branched or cyclic alkyl, and one or more of the carbon atoms may optionally be replaced with an O, S, or N.

The variable "X" represents an anion associated with the quaternary ammonium moiety of the present invention. The number and total charge of the negatively-charged anions associated with the quaternary ammonium ions of the present invention will vary depending on the pH of the mixture and on the anion of the acid or acids used for neutralization. The anions of the present invention may be any anion known to those of skill in the art, including monovalent, divalent and multivalent anions such as, nitrate, chlorate, tetrafluoroborate, perchlorate, hexafluorophosphate, permanganate, sulfite sulfonate, triflate, trifylamide, carboxylate, $F^-$, $Cl^-$, $Br^-$, $ClO_3^-$, $HSO_4^-$, $SO_4^{2-}$, $PO_4^{3-}$, and the like.

The variable "$Q^+$" as used herein refers to an organic quaternary ammonium moiety having a positively-charged nitrogen atom. The moiety preferably comprises aliphatic chains, but may nevertheless be water soluble. The positive charge associated with the quaternary ammonium moiety is generally unaffected by changes in pH. That is, the charge on the nitrogen center is not the result of simple protonation of an amine, so the pH of aqueous solutions of these salts may be adjusted over a wide range without causing the loss of the positive charge on the nitrogen center. Exemplary quaternary ammonium substituents of the invention are represented by formula (II):

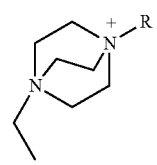

(II)

where R represents an aliphatic group, and which may be substituted. For example, R may be a substituted or unsubstituted alkyl, alkenyl, alkadienyl, alkatrienyl, alkapolyenyl, alkynyl, aromative, or polyether, and may have, for example, from 6-24 carbon atoms, such as 6, 8, 10, 12, 14, 16, or 18 carbon atoms. R may further be substituted, for example, with a second or further quaternary ammonium substituents such as those of formula II. The polycationic structure of formula II enhances permeability of the bacterial membrane and facilitates the antimicrobial action.

Other known quaternary ammonium moieties which may be used include those disclosed in U.S. Pat. No. 6,440,405, which are hereby incorporated by reference. Other quaternary ammonium moieties include those containing alkyl or aryl substituents on the quaternary nitrogen, with the alkyl or aryl substituents having less than 40 carbon atoms, and preferably less than 32 or 24 carbon atoms. For example, the quaternary nitrogen may be substituted by alkyl or aryl groups having from 1 to 32 carbon atoms, which may be linear or branched. Examples of such alkyl or aryl groups include phenyl, —($CH_2$)-phenyl, —($CH_2$)$_2$-phenyl, —($CH_2$)$_3$-phenyl, —($CH_2$)$_4$-phenyl, —($CH_2$)$_5$-phenyl, —($CH_2$)$_6$-phenyl, —($CH_2$)$_7$-phenyl, —($CH_2$)$_8$-phenyl, —($CH_2$)$_9$-phenyl, ($CH_2$)$_{10}$-phenyl, —($CH_2$)$_{11}$-phenyl, —($CH_2$)$_{12}$-phenyl, —($CH_2$)$_{13}$-phenyl, —($CH_2$)$_{14}$-phenyl, —($CH_2$)$_{15}$-phenyl, —($CH_2$)$_{16}$-phenyl, —($CH_2$)$_{17}$-phenyl, —($CH_2$)$_{18}$-phenyl, —($CH_2$)$_{19}$-phenyl, —($CH_2$)$_{20}$-phenyl, —($CH_2$)$_{21}$-phenyl, —($CH_2$)$_{22}$-phenyl, —($CH_2$)$_{23}$-phenyl, —($CH_2$)$_{24}$-phenyl, and chloromethyl.

Other quaternary ammonium substituents include those known in the art to exhibit antimicrobial properties.

The variable "S" represents a carbohydrate moiety, such as a monosaccharide, a disaccharide, a trisaccharide, an oligosaccharide, or a polysaccharide. In one embodiment of the invention, the functionalized glycodendrimer of the invention contains monosaccharides, which are independently selected from galactose, glucose, mannose, and lactose.

In one embodiment of the invention, the functionalized glycodendrimer is a compound of the formula (I), prepared from an $NH_2$-terminated polyamidoamine (PAMAM) dendrimer; n is from 1 to 6; L is —NH—C(S)—NH—$CH_2$—$CH_2$—O—$CH_2$—$CH_2$—O—, S is mannose, X is Chloride, and $Q^+$ is represented by the formula (II):

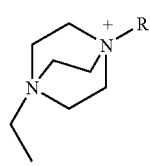

(II)

wherein R is alkyl. In this context, "alkyl" is a group of carbon and hydrogen atoms derived from an alkane molecule by removing one hydrogen atom. "Alkyl" may include saturated monovalent hydrocarbon radicals having straight, cyclic or branched moieties. R may further contain an optional carbon-carbon double or triple bond where said alkyl group comprises at least two carbon atoms. Alkyl groups may include any number of carbon atoms, however, for the purposes of the present invention, about 20 or less carbon atoms are preferred. Thus, alkyl groups having either 2, 3, 4, 5, 6, 7, 8, 9, 10, 11, 12, 13, 14, 15, 16, 17, 18, 19, or 20 carbons may be employed in the present invention. Of course, alkyl groups of longer length may also be employed.

In an exemplary embodiment of the invention, the functionalized glycodendrimer is a compound represented by the following formula (III):

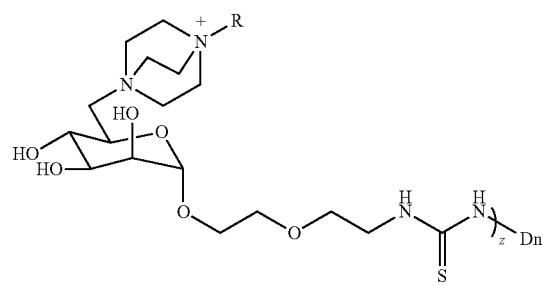

(III)

wherein R, z, D, and n are the same as defined in Formula I.

Synthesis of Quaternary Ammonium Functionalized Glycodendrimers

The advent of dendrimers represents a major breakthrough in synthetic chemistry. Dendrimers can be tailored to generate uniform or discrete functionalities and possess tunable inner cavities, surface moieties, sizes, molecular weights, and solvent interactions. The synthesis of dendrimers in known in the art.

Dendrimers can be synthesized by a convergent approach (Tomalia, et al. Macromolecules, 20, 1164 (1987)), or a divergent approach (Tang, et al. Bioconjugate Chem., 7, 703-714. (1996)). In the divergent approach, growth of dendrimers starts from a multi-functional core. Through a series of reaction and purification steps, dendrimers grow radially outwards. At different stages of the synthesis, dendrimers are identified by generations. As the generation increases, the number of functional groups, the size of the dendrimer, and the molecular weight of the dendrimer increase. At a certain stage of the synthesis, steric hindrance prevents one from achieving to obtain dendrimers, where the highest generation is synthesized. Commercially available dendrimers, such as polyamidoamine (PAMAM) from Dendritech Inc. (Midland, Mich., USA) and polypropylene imine (PPI) dendrimers from DSM (Geleen, Netherlands), are synthesized by the divergent approach. In the convergent approach, dendrons, as parts of dendrimers, are synthesized according to the divergent approach, and these dendrons are then coupled to a multifunctional core. The advantage of the convergent approach is that the chemistry of each dendron can be different, and distinct functional groups can be integrated into dendrimers at precise sites.

Dendrimers can offer a high local concentration of functional groups. A functionalized dendrimer is a dendrimer with surface groups that have been replaced with a chemical functional group. A surface group is the chemical groups at the terminal ends of the branches or backbone of a dendrimer. Surface groups can be for example —$NH_2$, —OH, —COOH, and —CN. For example, a polyamidoamine (PAMAM) dendrimer is terminated with —$NH_2$ surface groups. Chemical groups can be added to these surface groups such the resulting dendrimer is terminated by a —NH—W group wherein W is some functional chemical group. Functionalized dendrimers with biologically active groups results in an increased potency associated with the high local concentration. Once a dendrimer has been functionalized, they may be called functionalized dendrimers or modified dendrimers. The resulting functionalized dendrimer can be represented by Dn-(W)z, wherein D, n, and z are as previously described.

A dendrimer terminating with an $NH_2$ surface group may be coupled to a functional group, using an isothiocyanate intermediate, as described in Woller et al., Org. Lett. 4, 7-10 (2002) and J. Am. Chem. Soc. 125, 8820-8826 (2003), which are hereby incorporated by reference in their entireties. The reaction is illustrated in Scheme 1:

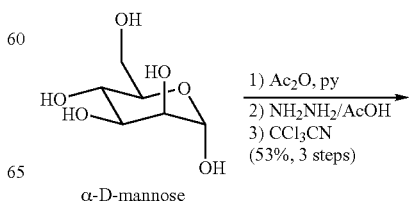

α-D-mannose

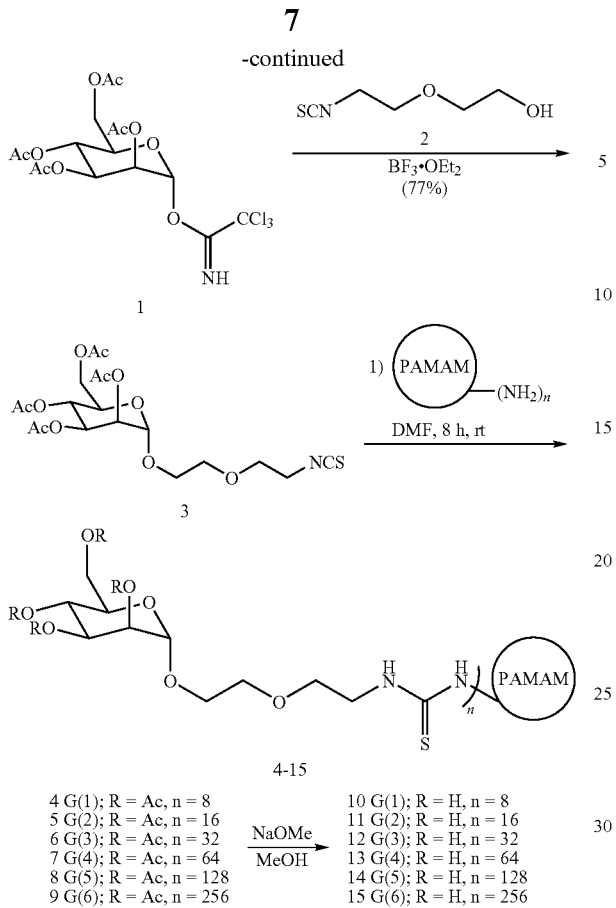

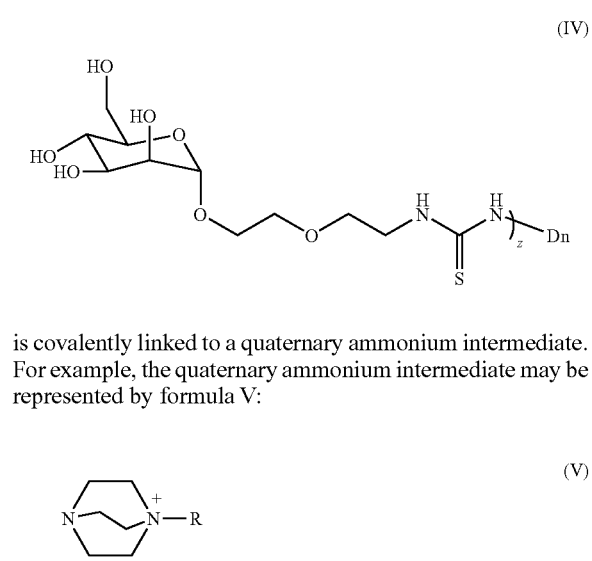

| 4 G(1); R = Ac, n = 8   | 10 G(1); R = H, n = 8   |
| 5 G(2); R = Ac, n = 16  | 11 G(2); R = H, n = 16  |
| 6 G(3); R = Ac, n = 32  | 12 G(3); R = H, n = 32  |
| 7 G(4); R = Ac, n = 64  | 13 G(4); R = H, n = 64  |
| 8 G(5); R = Ac, n = 128 | 14 G(5); R = H, n = 128 |
| 9 G(6); R = Ac, n = 256 | 15 G(6); R = H, n = 256 |

The reaction of a tertiary amine and the modified dendrimer finally results in a functionalized dendrimer. The reaction rate can be enhanced in polar solvents such as DMF. Elevated temperature also improves the reaction rate; however, high temperature also leads to the reverse reaction, the degradation of quaternary ammonium compounds. The reaction can be conducted in several solvents. The reaction rate is in the order of DMF>1-butanol>acetone. Sommer and coworkers also found similar rate dependence on solvent and that the relative quaternization rate in various solvents is 900:285:70:1 (DMF:methanol:butanol:hexane). Sommer et al., J. Org. Chem., 26, 824-828 (1971).

Compared to conventional polymers, the end groups of dendrimers play a more important role in determining their solubility. For example, the hydrophobically modified dendrimers, no matter what the interior structure of the dendrimers is, are soluble in hydrocarbons such as hexane and toluene. The solubility is primarily determined by the alkyl chain on the surface. Therefore, surface modification can lead to a significant difference in the solubility of the dendrimers. An appropriate solvent or solvent mixture must be selected if complete modification of the dendrimers is desirable.

Quaternary ammonium compounds are usually synthesized by the addition of an alkyl halide to a tertiary amine (Davis, B., Recent Developments in the Technology of Surfactants; Porter, M. R., Ed.; Elservier Applied Sciences: London, pp 70 (1990)). This reaction is reversible at high temperature, thus 30-80° C. is typically used for the synthesis. The quaternary ammonium salts are nearly insoluble in diethyl ether and benzene, sparingly soluble in acetone, and freely soluble in water and alcohol.

The quaternary ammonium functionalized glycodendrimers of the invention may be synthesized by reacting a hydroxyl group of the carbohydrate moiety of the glycodendrimers with a tertiary amine. TsCl, a highly reactive acid chloride derivative of the acid TsOH (tosic acid)—composition $CH_3C_6HSO_2Cl$ for TsCl—reacts with primary alcohols to generate esters of tosic acid. This renders the original carbinol carbon subject to nucleophilic substitution reaction by an incoming nucleophile (such as a tertiary amine) to attach that tertiary amine nitrogen to the original carbinol carbon (as a quaternary ammonium site), and break the original carbon-oxygen bond. Therefore, in a second step, the glycodendrimer intermediate of scheme 1 (represented by formula IV)

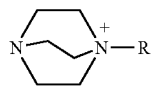

(IV)

is covalently linked to a quaternary ammonium intermediate. For example, the quaternary ammonium intermediate may be represented by formula V:

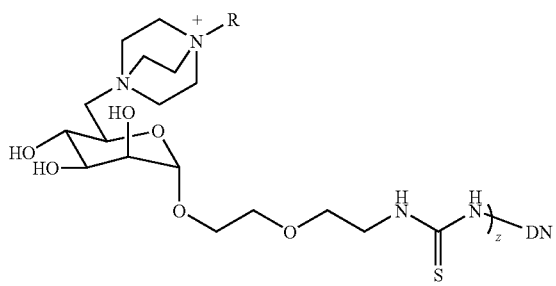

(V)

The reaction may be performed in a reaction inert solvent and in the presence of TsCl as described above, resulting in a compound of formula (III):

(III)

wherein R, n, and z are the same as defined above.

After the reaction, the resultant quaternary ammonium salts are repeatedly precipitated in large volumes of acetone and/or evaporation solvent. These precipitates are extremely hygroscopic. The precipitate is filtered, redissolved in a minimal amount of ethanol, and repeatedly stripped with anhydrous toluene to remove moisture. The samples are dried for about 120 hr at up to 65° C. (some glycodendrimers will decompose if heated above about 60° C.) in a vacuum oven and stored in a vacuum desiccator. Some samples appear to be crystalline while others appear amorphous. For the amorphous samples, recrystallization in acetone:methanol (9:1, v/v) may improve sample purity.

To further purify the samples, dialysis or diafiltration with a membrane with a 1000-2000 cut-off molecular weight is required. The dialysis process may be slow. A semi-continuous process called diafiltration, a combination of dialysis and ultrafiltration, may be used for purification. The diafiltration usually takes 2-3 days. To accelerate the dialysis step, ultrafiltration for some of the dendrimers may be used. The Centrifugal devices used were Millipore amicon ultra 4 mL 5000 $M_w$ and 10000 $M_w$ cutoff filters. For dialysis, dialysis membranes, diameter 11.5 mm, 1000 $M_w$ and 3500 $M_w$ cutoff, or microcentrifuge tubes, 1000 $M_w$ and 3500 $M_w$ cutoff may be used. The diafiltration may be stopped when the exit stream does not contain any tertiary amine or other small molecules detectable by a gas chromatography-mass spectrometer (GC-MS). The dendrimer biocides are also highly hygroscopic. Therefore, storage in vacuum desiccator is required.

The versatile chemistry allows for the preparation of a series of dendrimer biocides with different hydrophobes by using different tertiary amines, with different molecular weight, size and number of functional groups by using different generations of dendrimers, and with different counteranions by using different isothiocyanates. These dendrimer-biocides are soluble in alcohol, chloroform, and dimethylformamide; slightly soluble in water; and not soluble in tetrahydrofuran, toluene, and acetone.

Generally speaking, the compounds of the present invention are particularly effective where the target sites are microbial cell walls and/or cell membranes. First, since there are many carbohydrate/quaternary ammonium substituents on the dendrimer, the invention can lead to glycoside clustering where the dendrimer is sufficiently large to bind multivalently to the target. In this respect, dendrimers having a size of from about 20 to about 35 angstroms are desirable. Further, the polycationic structure of the present invention improves the permeability of the bacterial membrane and facilitates the antimicrobial action.

The functionalized dendrimers of the present invention may find use in any number of applications that require a potent biocide/antimicrobial agent.

Pharmaceutical Compositions

The present invention provides a pharmaceutical composition comprising a therapeutically effective amount of a quaternary ammonium functionalized glycodendrimer according to the invention, and a suitable pharmaceutical carrier therefor. The functionalized glycodendrimer of the present invention is typically present in an amount sufficient to reduce inflammation, to thereby produce a therapeutic effect. The invention thus provides a quaternary ammonium functionalized glycodendrimer according to the invention for use as a medicament, and to practice the methods of the invention.

The pharmaceutical compositions useful for practicing the invention may be administered to deliver a dose of between 1 ng/kg/day and 100 mg/kg/day.

Pharmaceutical compositions that are useful in the methods of the invention may be administered systemically in oral solid formulations, ophthalmic, suppository, aerosol, and topical or other similar formulations. Such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate glycodendrimer according to the methods of the invention.

Compounds, which are identified using any of the methods described herein, may be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art. As used herein, the term "pharmaceutically acceptable carrier" means a chemical composition with which the active ingredient may be combined and which can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions, are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats and dogs, and birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use. Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged; or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically dosages of the compound of the invention which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Utilities

The present invention provides methods of controlling the growth of a microorganism by diminishing proliferation of and/or killing microorganisms such as bacteria, spores, yeast, fungi, mold and multicellular microorganisms. Exemplary microorganisms are listed in Table 1, as well as exemplary infections for which the present invention finds use. Quaternary ammonium functionalized glycodendrimers provided herein are contemplated to be effective against these and other microorganisms. The quaternary ammonium functionalized glycodendrimers of the current invention are particularly intended to be employed in connection with each of the materials, tissues and sites recited in Table 1. The present invention is also effective for reducing the contamination of spores, which are small primitive reproductive bodies, or resistant resting cells, typically unicellular. Exemplary spores are the dustlike asexual reproductive bodies of fungi, or *B. anthracis*, or anthrax, spores.

TABLE 1

Partial list of infections

| Infection or disease | Common bacterial species |
|---|---|
| Human disease | |
| Dental caries | Acidogenic Gram-positive cocci (e.g. *Streptococcus*) |
| Periodontitis | Gram-negative anaerobic oral bacteria |
| Otitis media | Nontypable strains of *Haemophilus influenzae* |
| Musculoskeletal infections | Gram-positive cocci (e.g. staphylococci) |
| Necrotizing fasciitis | Group A streptococci |
| Biliary tract infection | Enteric bacteria (e.g. *Escherichia coli*) |
| Osteomyelitis | Various bacterial and fungal species--often mixed |
| Native valve endocarditis | Viridans group streptococci |
| Cystic fibrosis pneumonia | *P. aeruginosa* and *Burkholderia cepacia* |
| Meloidosis | *Pseudomonas pseudomallei* |
| Medical device related infection | |
| ICU pneumonia | Gram-negative rods |
| Sutures | *Staphylococcus epidermidis* and *S. aureus* |
| Exit sites | *S. epidermidis* and *S. aureus* |
| Arteriovenous shunts | *S. epidermidis* and *S. aureus* |
| Schleral buckles | Gram-positive cocci |
| Contact lens | *P. aeruginosa* and Gram-positive cocci |
| Uurinary catheter cystitis | *E. coli* and other Gram-negative rods |
| Peritoneal dialysis peritonitis | A variety of bacteria and fungi |
| Endotracheal tubes | A variety of bacteria and fungi |
| Hickman catheters | *S. epidermidis* and *C. albicans* |
| Central venous catheters | *S. epidermidis* and others |
| Mechanical heart valves | *S. aureus* and *S. epidermidis* |
| Vascular grafts | Gram-positive cocci |
| Biliary stent blockage | A variety of enteric bacteria and fungi |
| Orthopedic devices | *S. aureus* and *S. epidermidis* |

The present invention provides a method of controlling the growth of a microorganism comprising exposing a microorganism to a quaternary ammonium functionalized glycodendrimer of the present invention. For example, a microorganism may be exposed to the functionalized glycodendrimer of the present invention by treating a surface with the quaternary ammonium functionalized glycodendrimer, where the surface is contaminated with or may be subsequently contaminated with a microorganism. Any surface at risk of contamination may be used in conjunction with the present invention. Typically, the method involves bringing a microorganism into sufficient proximity to the functionalized glycodendrimer of the present invention to cause an effect on the growth or proliferation of the microorganism. This will generally involve physical interactions between the microorganism and the functionalized glycodendrimer. In addition to those in Table I, the glycodendrimer of the present invention is effective on microorganisms such as *Salmonella* spp., *Escherichia coli, Enterobacter* spp. (such as *Enterobacter aerogenes* and *Enterobacter cloacae*), *Proteus vulgaris, Bacillus cereus, Micrococcus luteus*, and *Staphylococcus aureus*.

Functionalized dendrimers of the present invention may be employed in solution (or initially in solution which may dessicate or carrier solvent may evaporate for example for coatings, paint and the like) at an effective concentration to control the growth of microorganisms. The functionalized dendrimers of the present invention may be employed at a wide variety of concentrations. Concentration of up to 100% may be used. Otherwise functionalized dendrimer of the present invention can be effective at concentrations from 1 ppm to concentration in excess of 10%. Effective minimum concentrations of functionalized dendrimers of the present invention against common bacteria is contemplated to be in concentrations 5 ppm to 1 to 2%. Preferred concentrations are from 10 ppm to 200 ppm. More preferred is 20 ppm to 100 ppm. The exact concentration will depend upon somewhat on the desired use (e.g., employment as a pre-surgical handwash disinfectant, coating for a biomaterial or otherwise prosthetic device for internal use, or element of an industrial-use biocidal coating). Elements for the formulations of functionalized dendrimers described herein are well known and are described, for example, in U.S. Pat. Nos. 6,030,632, 5,869, 073, 6,022,551; 5,906,808; 5,776,430; 5,597,561; 5,244,666; and 5,164,107, each of which is herein incorporated by reference.

In addition to exposure/interactions in solution, the present method also encompasses solid phase exposure/interaction, and liquid/solid phase exposure. For example, liquid/solid phase exposure of the quaternary ammonium functionalized glycodendrimer of the present invention to one or more microorganisms may involve using the quaternary ammonium functionalized glycodendrimer in a spray mixed with a suitable liquid carrier. Spray as used herein refers to the quaternary ammonium functionalized glycodendrimer of the present invention with or without a suitable carrier liquid applied as a liquid stream, fine vapor, mist, small drops, aerosol, or non-aerosol. This spray can then be used to expose a microorganism to a quaternary ammonium functionalized glycodendrimer in liquid form. The spray could be used for example to control the growth of microorganisms in or on clothing and surfaces. Particularly preferred compounds in this respect are dendrimer generation G(3).

The functionalized glycodendrimers are also intended for industrial as well as medical and home use applications including but not limited to elements of protective coatings such as paints, handwash formulations, means for use in ointments and related topical applications, cosmetics, cleaning and/or disinfectant/sanitation products, and sanitation of recreational water such as swimming pools and spas. The functionalized glycodendrimers are also intended to be used as a component in coating filters and fibers such as cotton as a new fabric to make, for example, uniforms for the military. The functionalized glycodendrimers are also effective against Anthrax spore. The dendrimer biocides of the present invention are nonreactive and are virtually nontoxic to human skin.

The functionalized glycodendrimers can also be immobilized on the surface of materials to create efficient antimicrobial environments in a wide variety of applications including garments for protective use as well as biomaterials and prosthetic devices for medical use. For example quaternary ammonium functionalized glycodendrimer of the present invention can be immobilized to polymers, glass, and metals. Polymers can be for example polyurethanes. Other examples include polystyrene, rubber, polyethylene, polypropylene, and engineering plastics. Immobilized on the surface is defined as attachment of functionalized glycodendrimers to a surface by covalent bonding, ionic interaction, coulombic interaction, hydrogen bonding, crosslinking (e.g., as crosslinked (cured) networks) or as interpenetrating networks, for example.

The present invention further provides a glycodendrimer of the present invention for use as a medicament, and further provides methods of treatment and/or prevention of various diseases and conditions comprising administering an effective amount of a glycodendrimer of the invention to a subject, generally a human, in need of such treatment. The invention includes the use of the quaternary ammonium functionalized glycodendrimers of the invention in veterinary medicine.

The compounds of the invention are particularly useful in the treatment and/or prevention of, for example, sepsis, severe sepsis, septic shock, the systemic inflammatory response associated with sepsis, rheumatological disease, eczema, psoriasis, contraction of tissues during wound healing, excessive scar formation during wound healing in animals and human. Rheumatological and inflammatory conditions include rheumatoid arthritis, juvenile chronic arthritis, psoriatic arthritis, reactive arthritis occurring after an infection, active ankylosing spondylitis, arthritis associated with inflammatory bowel disease, Behcet's disease including Behcet's disease with panuveitis and/or retinal vasculitis, psoriasis, inflammatory bowel disease (Crohn's disease, ulcerative colitis).

The term "sepsis syndrome" refers to sepsis plus impaired organ perfusion. The spectrum of clinical syndromes ranging from bacteremia to sepsis to severe sepsis to septic shock to refractory septic shock and to the systemic inflammatory response syndrome represents a continuum in which localized inflammation is at one end with a severe generalized inflammatory response leading to multi-organ failure being at the other end of the spectrum. In severe cases, death can occur within a few hours.

In a preferred aspect of the present invention, the quaternary ammonium functionalized glycodendrimers have activity against the systemic inflammatory response syndrome that is associated with bacterial or fungal infections. A glycodendrimer of the present invention may be used to treat sepsis caused by the lipopolysaccharide from gram negative bacteria, or a superantigen toxin from a gram positive bacterium, for example the severe sepsis, the septic shock or the systemic inflammatory response associated with sepsis caused by the lipopolysaccharide from gram negative bacteria, or a superantigen toxin from a gram positive bacterium.

The compounds and formulations of the invention are suitable for administration intravenously, orally, intraperitoneally, topically (skin), buccal, rectally, to the surface of the skin, transdermal (slow release preparation), subcutaneously, intramuscularly, intranasally, by aerosol, by pulmonary administration, and directly to the eye.

Compounds of the present invention can also be used in combination with existing and accepted therapeutic approaches as adjuvant therapy. For example, in the sepsis syndrome they could be used with antibacterial drugs or antifungal drugs. In rheumatoid arthritis and related conditions, Behcet's disease, inflammatory bowel disease and psoriasis, they could be used with steroids and disease modifying drugs such as methotrexate or disease modifying therapeutic antibodies.

A further advantage of the quaternary ammonium functionalized glycodendrimers of the present invention is that they are large molecules. Tissue based sites of inflammation are more permeable to circulating molecules and cells than is healthy tissue, irrespective of what triggers the inflammatory response. Large molecules accumulate in areas of inflammation more rapidly that they do in normal tissue. The quaternary ammonium functionalized glycodendrimers of the present invention will therefore tend to accumulate at sites of inflammation.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Reference Example 1

Synthesis of G3 Glycodendrimer

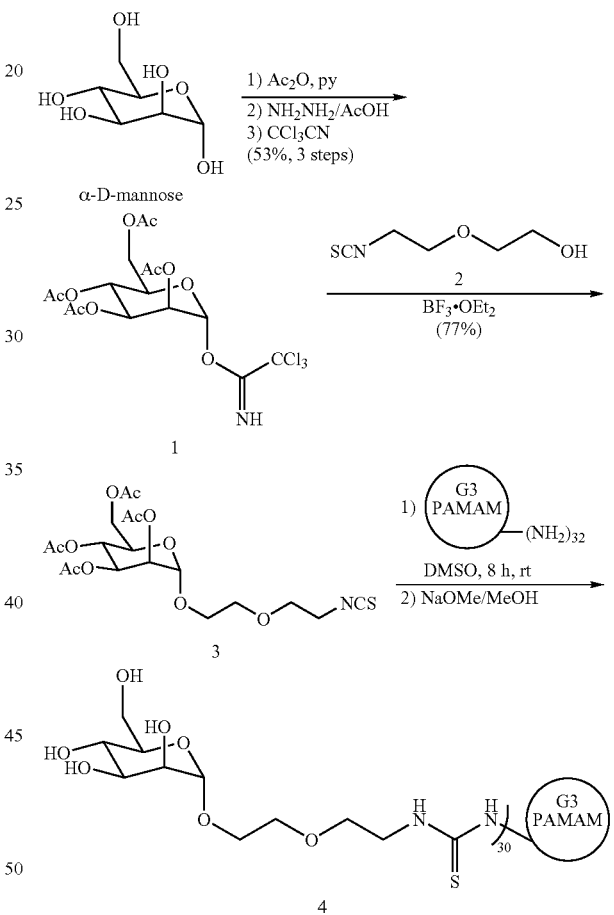

Mannose-functionalized dendrimers 4 were synthesized as shown in Scheme 1. Peracetylation of D-mannose followed by selective deprotection and activation at the anomeric position afforded trichloroacetimidate 1. Coupling of 1 with the isothiocyanato alcohol 2 using $BF_3 \cdot OEt_2$ gave the mannose monomer 3. Addition of 3 to the dendrimer followed by global deacetylation and dialysis (water/cellulose tube, MW cutoff 1000 g/mol) afforded 4 in purified form. For a more detailed description of the reactions, see Woller, E. K.; Walter, E. D.; Morgan, J. R.; Singel, D. J.; Cloninger, M. J. "Altering the Strength of Lectin Binding Interactions and Controlling the Amount of Lectin Clustering Using Mannose/hydroxyl Functionalized Dendrimers" *J. Am. Chem. Soc.* 2003, 125, 8820-8826 and Woller, E. K.; Cloninger, M. J. "The Lectin-binding Properties of Six Generations of Mannose-functionalized Dendrimers". *Org. Lett.* 2002, 4, 7-10., which are incorporated herein by reference.

Reference Example 2

Coupling of Quaternary Ammonium Groups to Carbohydrates

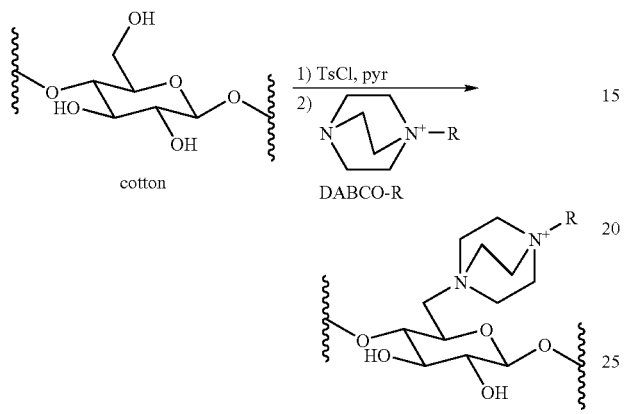

For a more detailed description of the steps of synthesis of the reference compound, see Abel, T., Cohen, J.-L. I., Engel, R., Filshtinskaya, M., Melkonian, A., Melkonian, K. "Preparation and investigation of antibacterial carbohydrate-based surfaces" Carbohydrate Res. 2002, 337: 2495-2499, which is incorporated herein by reference.

Example 1

Synthesis of Quaternary Ammonium Functionalized Glycodendrimer

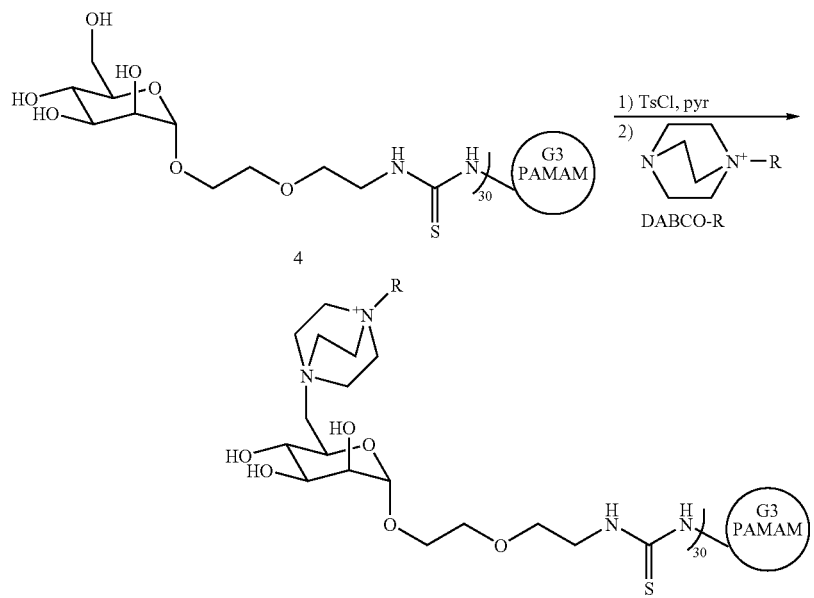

R = C16 alkyl chain

What is claimed is:

1. A quaternary ammonium functionalized glycodendrimer comprising a plurality of carbohydrate and quaternary ammonium substituents covalently linked to a dendrimer, the quaternary ammonium functionalized glycodendrimer having the formula:

$$(Q^+\text{-}S\text{-}L)z\text{-}DnX^- \qquad (I)$$

wherein:

D is a dendrimer;

n is the generation number of the functionalized dendrimer and selected from 1, 2, 3, 4, 5, 6, 7, 8, 9, 10, 11, 12, 13, 14, and 15;

z is an integer less than or equal to $2^{(n+2)}$;

L is a linking group;

$Q^+$ represents a quaternary ammonium moiety; and

S represents a carbohydrate moiety.

2. The glycodendrimer of claim 1, wherein the dendrimer is of a generation greater than 4.

3. The glycodendrimer of claim 1, wherein the dendrimer is selected from the group consisting of a polyamidoamine dendrimer, a polylysine-based dendrimer, a polyethylene oxide-based dendrimer, a silicon-based dendrimer, a polypropylene imine dendrimer, a polyether-based dendrimer, a polyethylene oxide-based hyperbranched polymer, a polyglycerol-based hyperbranched polymer, a silicon-based hyperbranched polymer, and hyperbranched polyols and hybrane.

4. The glycodendrimer of claim 1, wherein the carbohydrate substituents are each independently selected from galactose, glucose, mannose and lactose.

5. The glycodendrimer of claim 1, wherein the quaternary ammonium substituents are represented by the formula (II):

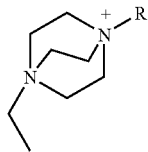
(II)

wherein R represents an aliphatic group.

6. The glycodendrimer of claim 5, wherein R is alkyl, alkenyl, alkadienyl, alkatrienyl, alkapolyenyl, alkynyl, aromative, or polyether, and wherein R may have a terminal-functional group.

7. The glycodendrimer of claim 6, wherein R has a terminal functional group selected from $—NH_2$, —OH, —COOH, or —CN.

8. The glycodendrimer of claim 1, wherein each linking group L is independently selected from $—NH—C(S)—NH—CH_2—CH_2—O—CH_2—CH_2—O—$, $—CO—NH—CH_2—CH_2—$, $—CO—NH—CH_2—$, $—CO—NH—CH_2—CH_2—CH_2—$, $—CO—NH—CH_2—CH_2—CH_2—CH_2$, $—CO—NH—CH_2—CH_2CH_2—CH_2CH_2—$, $—CO—NH$-Phenyl-$CH_2—$, $—CO—NH—CH_2—CH_2—O—CH_2—CH_2—$, $—(CH_2)—$, $—(CH_2)_2—$, $—(CH_2)_3—$, $—(CH_2)_4—$, $—(CH_2)_5$, $—(CH_2)_6—$, $—(CH_2)_7—$, $—(CH_2)_8$, $—(CH_2)_9$, $—(CH_2)_{10}—$, $—(CH_2)_{11}—$, $—(CH_2)_{12}—$, $—(CH_2)_{13}—$, $—(CH_2)_{14}$, $—(CH_2)_{15}$, $—(CH_2)_{16}$, $—(CH_2)_{17}$, $—(CH_2)_{18}$, $—(CH_2)_{19}$, $—(CH_2)_{20}—$.

9. The glycodendrimer of claim 1, wherein n is from 4-8.

10. The glycodendrimer of claim 9, wherein n is 6.

11. The glycodendrimer of claim 1, wherein X is one or more of chloride, bromide, sulfate, nitrate, chlorate, tetrafluoroborate, perchlorate, hexafluorophosphate, permanganate, and sulfite.

12. The glycodendrimer of claim 1, wherein each carbohydrate moiety S is independently selected from the group consisting of a monosaccharide, a disaccharide, a trisaccharide, and an oligosaccharide.

13. The glycodendrimer of claim 1, wherein the carbohydrate moiety is mannose.

14. The glycodendrimer of claim 1, wherein D is an $NH_2$ terminated polyamidoamine (PAMAM) dendrimer.

15. The glycodendrimer of claim 1, wherein L is $—NH—C(S)—NH—CH_2—CH_2—O—CH_2—CH_2—O—$ and X is Chloride.

16. The glycodendrimer claim 5, wherein R is a linear alkyl group having 8 to 24 carbon atoms.

17. A formulation comprising the glycodendrimer of claim 1 and a pharmaceutically acceptable carrier.

18. A method for controlling the growth of a microorganism comprising exposing said microorganism to a quaternary ammonium functionalized glycodendrimer of claim 1.

19. The method of claim 18, comprising, treating a surface with said quaternary ammonium functionalized glycodendrimer, said surface being contaminated with said microorganism.

20. The method of claim 18, wherein said microorganism is selected from the group consisting of acidogenic Gram-positive cocci, Gram-negative anaerobic oral bacteria, Group A streptococci, enteric bacteria, Gram-negative rods, and Gram-positive cocci.

21. The method of claim 20, wherein said microorganism is *Streptococcus, Staphylococci, Haemophilus influenzae, Escherichia coli, P. aeruginosa, Burkholderia cepacia, Pseudomonas pseudomallei, C. albicansm, Staphylococcus epidennidis*, or *S. aureus*.

22. The method of claim 20, wherein said microorganism is a spore.

23. The method of claim 20, wherein said spore is a *B. anthracis* spore.

24. The method of claim 18, wherein said quaternary ammonium functionalized glycodendrimer is immobilized on a surface, said surface being subsequently exposed to said microorganism.

25. The method of claim 24 wherein said surface is a polymer, glass, or metal surface.

26. The method of claim 25, wherein said polymer is selected from the group consisting of polyurethane, polystyrene, polyethylene, and polypropylene.

27. The method of claim 19, wherein said quaternary ammonium functionalized glycodendrimer is applied to said surface as a spray.

28. The method of claim 24, wherein said quaternary ammonium functionalized glycodendrimer is incorporated into a coating.

29. A method for treating a subject to treat a disease or condition associated with inflammation comprising administering to the subject an amount of a glycodendrimer of claim 1 in an amount that is effective to treat the disease or condition.

30. The method of claim 29, wherein the disease or condition is selected from the group consisting of severe sepsis, septic shock, the systemic inflammatory response associated with sepsis, rheumatological disease, eczema, psoriasis, contraction of tissues during wound healing, excessive scar formation during wound healing.

31. The method of claim 29 wherein the disease is selected from the group consisting of rheumatoid arthritis, juvenile chronic arthritis, psoriatic arthritis, reactive arthritis occurring after an infection, acute ankylosing spondylitis, arthritis associated with inflammatory bowel disease, Behcet's disease including Behcet's disease with panuveitis and/or retinal vasculitis, inflammatory bowel disease, Crohn's Disease, and ulcerative colitis.

32. The method of claim 30, wherein the disease or condition is severe sepsis, septic shock, or systemic inflammatory response associated with sepsis is caused by a lipopolysaccharide from a gram negative bacterium.

33. The method of claim 30 wherein the severe sepsis, septic shock, or systemic inflammatory response associated with sepsis is caused by a superantigen toxin from a gram positive bacterium.

* * * * *